(12) United States Patent
Kanda et al.

(10) Patent No.: US 6,248,070 B1
(45) Date of Patent: Jun. 19, 2001

(54) ULTRASONIC DIAGNOSTIC DEVICE

(75) Inventors: Ryoichi Kanda; Tetsuya Kawagishi, both of Tochigi-ken (JP)

(73) Assignee: Kabushiki Kaisha Toshiba, Kawasaki (JP)

( * ) Notice: Subject to any disclaimer, the term of this patent is extended or adjusted under 35 U.S.C. 154(b) by 0 days.

(21) Appl. No.: 09/406,770

(22) Filed: Sep. 28, 1999

(30) Foreign Application Priority Data

Nov. 12, 1998 (JP) .................................................. 10-322259

(51) Int. Cl.⁷ ....................................................... A61B 8/00

(52) U.S. Cl. ........................................... 600/443; 128/916

(58) Field of Search .................................... 600/437, 443, 600/447, 450, 441; 128/916; 73/625, 626; 367/7, 11; 607/122, 9, 116, 119

(56) References Cited

U.S. PATENT DOCUMENTS

| | | | |
|---|---|---|---|
| 5,410,516 | 4/1995 | Uhlendorf et al. | |
| 5,433,198 | * 7/1995 | Desai | 607/122 |
| 5,443,489 | * 8/1995 | Ben-Haim | 607/115 |
| 5,615,680 | 4/1997 | Sano | |
| 5,871,019 | * 2/1999 | Belohlavek | 128/916 |

* cited by examiner

Primary Examiner—Marvin M. Lateef
Assistant Examiner—Ali M. Imam
(74) Attorney, Agent, or Firm—Oblon, Spivak, McClelland, Maier & Neustadt, P.C.

(57) ABSTRACT

An ultrasonic diagnostic apparatus including an ultrasonic probe, and a transmitter/receiver section for scanning a three dimensional region of a detected object with ultrasonic beams by driving the ultrasonic probe and receiving echo signals reflected from an object within the three dimensional region. An organ of the object is detected and three dimensional figure image data depicting a figure of the detected organ in the three dimensional region are formed based on the received echo signals. Also determined from the received echo signals is a function of the detected organ, for example by obtaining and thresholding tissue Doppler image data or harmonic image data, and based on the determined function, three dimensional functional image data depicting the function of the detected organ in the three dimensional region are formed. The three dimensional figure image data are displayed by a wire frame method, a bull's eye map method and/or a semi-transparent surface model method. The displayed three dimensional figure image of the detected organ is combined with display of the functional image of the organ, with neither displayed image obstructing the other displayed image so that the figure image of the organ can be utilized as a positioning guide for selection of the position of the functional image of the organ.

21 Claims, 3 Drawing Sheets

ULTRASONIC DIAGNOSTIC DEVICE

CROSS REFERENCE TO RELATED APPLICATIONS

This application claims benefit of priority to Japanese Patent Application No. 10-322259 filed Nov. 12, 1998, the entire disclosure of which is incorporated by reference herein.

BACKGROUND OF THE INVENTION

1. Field of the Invention

The present invention relates to an ultrasonic diagnostic apparatus for scanning a three dimensional region of a detected object and producing three dimensional image data of a figure and function of a specific internal organ, such as the heart, based on received signals obtained from the scanning.

2. Discussion of the Background Art

Recently, an ultrasonic diagnostic apparatus can display an image to provide functional information about an internal organ, specifically the heart. For example, one idea involves a method to determine a condition of ischemic heart disease by detecting volume information of an interior wall movement of the heart muscle. This has been known as the tissue Doppler image method, in which speed of a heart muscle is displayed with brightness and color changing in accordance with elapsed figure deforming. In the tissue Doppler imaging (TDI) method, a portion displayed without brightness and color can be judged as a portion which is not actuating so much such and may evidence an infarction of the heart muscle.

On the other hand, there is an idea for displaying an ultrasonic contrast medium image injected into a detected object by a harmonic imaging (HI) method and other methods. In harmonic imaging, it is possible to detect a portion into which the ultrasonic contrast medium does not flow so much with blood, thereby to obtain a visualization of perfusion.

Further, there recently has been developed an ultrasonic diagnostic apparatus for collecting and displaying three dimensional figure information in an organism, such as a B-mode image, in real time. In order to proceed in real time, there is employed a multi-direction simultaneous receiving technique for transmitting a broadly spreading wide ultrasonic beam and simultaneously forming a plurality of beams of a directivity different from each other as receiving beams.

However, there still exists a problem to be solved in order to form a three dimensional functional image for showing functions of the heart by the TDI method, the HI method and so on, Unless an unusual portion in the heart, where an infarction of the heart exists and reflux of blood occurs, can be detected, the imaging result can not be utilized for diagnosis. In order to solve the problem, a two dimensional functional image has been overlapped on a two dimensional figure image in the field of two dimensional techniques.

In a field of the three dimensional technique, if a three dimensional functional image is overlapped on a three dimensional figure image in a way similar to the two dimensional technique, one image interrupts viewing of the other image, and vice versa. That is, a part of the functional image overlapped with the figure image and a part of the figure image overlapped with the functional image mutually interrupt viewing one image. As the result, a location of an unusual portion can not be specified and the likelihood of missed detection of the unusual portion is increased.

SUMMARY OF THE INVENTION

An object of the present invention is to provide an ultrasonic diagnostic apparatus in which a three dimensional display method is employed, wherein a figure image of an internal organ such as a heart is operated as a positioning guide in order to be combined with a functional image without either image interrupting the other.

This and other objects are achieved according to the present invention by providing a novel ultrasonic diagnostic apparatus including an ultrasonic probe, and a transmitter/receiver section for scanning a three dimensional region of a detected object with ultrasonic beams by driving the ultrasonic probe and receiving echo signals reflected from an object within the three dimensional region. Based on the received echo signals, an organ of the object is detected and three dimensional figure image data depicting a figure of the detected organ in the three dimensional region are formed. Also determined from the received echo signals is a function of the detected organ, for example by obtaining and thresholding tissue Doppler image data or harmonic image data, and based on the determined function, three dimensional functional image data depicting the function of the detected organ in the three dimensional region are formed. The three dimensional figure image data are displayed combined with the three dimensional functional image data.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION OF THE PREFERRED EMBODIMENTS

Figure 1:
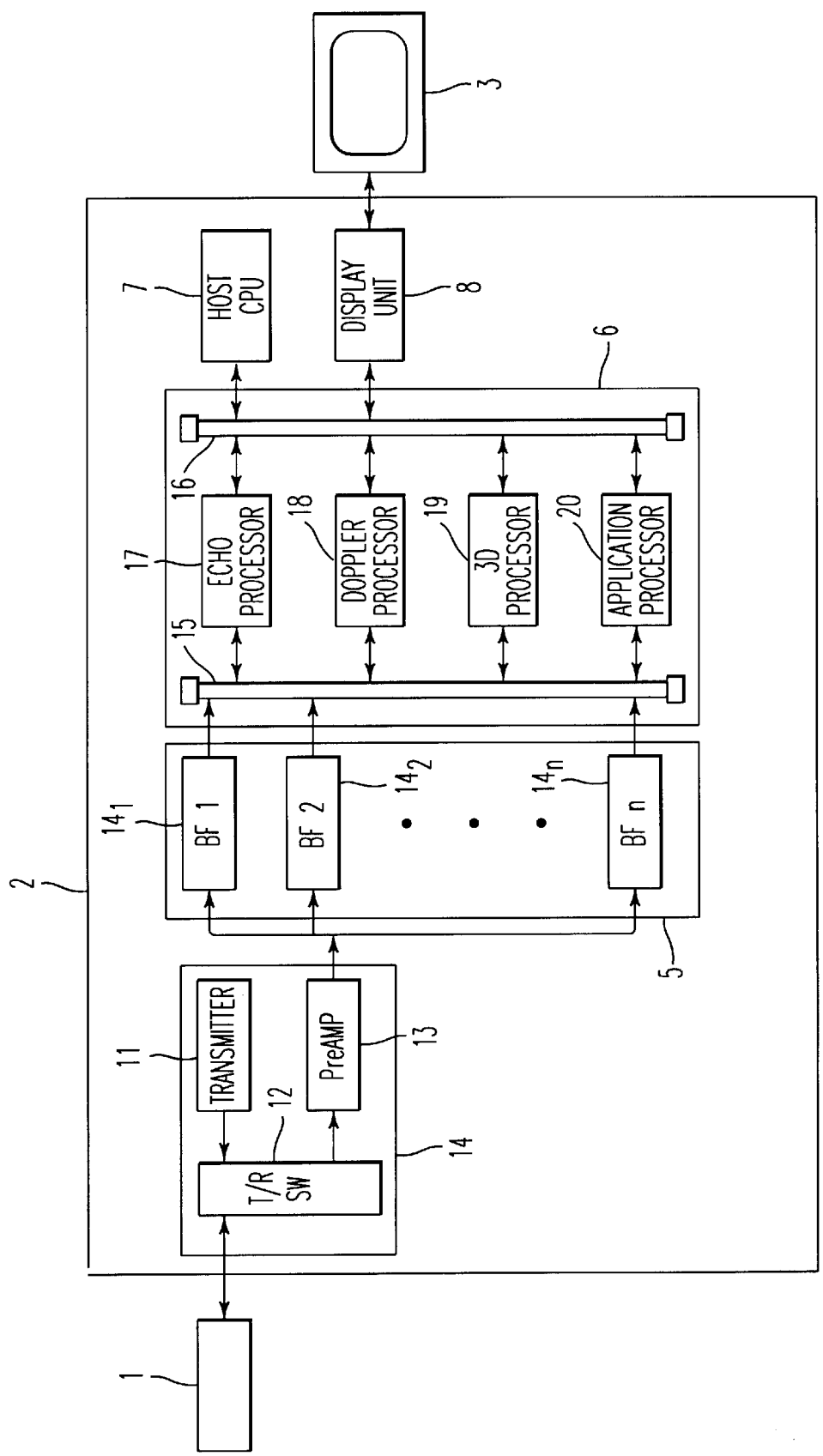
FIG. 1 is a block diagram of an embodiment of an ultrasonic diagnostic apparatus according to the present invention.

Referring now to the drawings, wherein like reference numerals designate identical or corresponding parts throughout the several views, and more particularly to FIG. 1 thereof, FIG. 1 shows a block diagram of an embodiment of an ultrasonic diagnostic apparatus according to the present invention, including an ultrasonic probe 1, a main body member 2 and a display member 3. The ultrasonic probe 1 has a plurality of piezoelectric transducers arranged in a matrix form of a two dimensional array and is capable of inter-converting between electric signals and sound signals and electronically scanning at high-speed a three dimensional region of an interior of a detected object with ultrasonic beams.

The main body member 2 includes a transmitting/receiving unit 4, a digital beam former unit 5, a signal processing unit 6, a host CPU 7 and a display unit 8. The transmitting/receiving unit 4 includes a T/R switch 12, a transmitter 11 and a preamplifier 13. When the transmitting/ receiving unit 4 transmits an ultrasonic beam, the ultrasonic probe 1 is connected to the transmitter 11. When the transmitting/receiving unit 4 receives ultrasonic beams, the ultrasonic probe 1 is connected to the preamplifier 13.

The transmitter 11 includes a clock generator, a divider, a transmitting delay circuit and a pulsar (not shown). Clock pulses generated by the clock generator are changed to late pulses at about 6 KHz. The late pulses are transmitted to the pulsar through the transmitting/delay circuit in order to generate high frequency high voltage pulses and drive the piezoelectric transducers mechanically. A generated ultrasonic beam is reflected on a boundary of acoustic impedance in the detected object and the reflected beams return to the ultrasonic probe 1 and drive the piezoelectric transducers mechanically. Thus, an electric signal is produced in each piezoelectric transducer. After the preamplifier 13 amplifies the electric signal, the signal is transmitted to the digital beam former unit 5 in order to perform phase-addition, whereby an echo signal having directivity is produced.

An ultrasonic beam is widened intentionally by delay controlling a voltage pulse given to each piezoelectric transducer in order to advance real time characteristic by shortening three dimensional scanning (volume scanning) period and improving scanning times (volume rate) in the three dimensional region per each second. A plurality of echo signals having the respective directivities (i.e., N) are produced by transmitting the widened ultrasonic beam each time. To accomplish a multi-direction simultaneous receiving method, the digital beam former unit 5 includes N digital beam formers $14_1$~$14_N$, each of which performs phase-addition in accordance with a respective phase pattern.

The signal processing unit 6 includes four processors 17 through 20 connected to buses 15 and 16.

Based on the echo signal from the digital beam former unit 5, the echo processor 17 forms B-mode image data to provide figure information about tissue structure and harmonic image data to show heart functions in case of injecting ultrasonic contrast medium. Both B-mode image data and harmonic image data are utilized to detect an envelope of the echo signal. In the HI method, a harmonic component (double the reference frequency component, i.e., the second harmonic of the echo signal from the object) which frequently occurs upon reflection by the ultrasonic contrast medium is extracted from the echo signal. On the other hand, in the B-mode imaging method, a harmonic component extraction process is not performed.

In the harmonic imaging (HI) method, a portion in which the ultrasonic contrast medium flows with blood is emphasized as a second harmonic sound source, which is displayed, and a reflux portion in which the ultrasonic contrast medium is not flown with blood, and from which no second harmonic signal is reflected, is not displayed. Thereby, the reflux portion can be found effectively and perfusion (the amount of blood) can be detected.

The Doppler processor 18 is a color flow-mapping unit. Firstly, Doppler signals having frequencies changed by the echo signal detected at a perpendicular phase by the digital beam former unit 5 are picked up. A specific frequency component of the picked up Doppler signals are passed through a MTI filter, and the frequency of the filtered signals is then detected by an auto correlation device. The computing member calculates average speed, deflocculation and power from the frequency.

By controlling the frequency band of the MTI filter, a high frequency band mode for mainly displaying blood fluid (image data obtained by this mode are called "blood fluid Doppler image data") and a low frequency band mode, also known as a tissue Doppler imaging (TDI) mode, for mainly displaying movement of an organ such as heart muscle can be switched.

The 3D processor 19 forms three dimensional figure image data, for example, a three dimensional figure of interior walls of left-side chambers of the heart in a wire frame model, a semi-transparent surface model, based on the produced B-mode image data. In order to form three dimensional figure image data, it is necessary to extract border points at the interior walls of the left-side chambers. To extract the border points, various methods can be considered. For example, one general method is to compare brightness radiately transmitted from a center of gravity at each point with a threshold value (e.g.,. averaged brightness on a radiate beam). A point at which the brightness first exceeds the threshold value is recognized as a border point of an interior wall of leftside chambers.

The 3D processor 19 extracts from the harmonic image data produced by the echo processor 17 a portion having relatively low brightness although the ultrasonic contrast medium is injected, that is, a portion in which brightness is not so much enhanced, by comparison with a threshold level. Three dimensional image data of the extracted portion is formed in a surface model. In the three dimensional image data, a portion into which the ultrasonic contrast medium is not flown is also displayed. Thereby, it is effective to find a reflux portion.

From tissue Doppler image data produced by the Doppler processor 18, the 3D processor 19 extracts a portion having relatively low speed by comparing with a threshold level and forms three dimensional image data for display of the extracted portion in the surface model. In the three dimensional image, a portion not actuating so much is also displayed. Thereby, it is effective to find an infarction of the heart muscle.

A function of a heart can be observed from the harmonic image and the tissue Doppler image. The image is called as a functional image compared to a figure image for showing a tissue structure.

Further, the 3D processor 19 combines the above described three dimensional figure image data with an optional three dimensional functional image data by matching a point of the three dimensional figure image data and the corresponding point of three dimensional functional image data. The combined image of the three dimensional figure image data and the three dimensional functional image data is displayed on the display unit 8 through a display device 3.

The application processor 20 is capable of processing a display mode and measurement.

Figure 2:
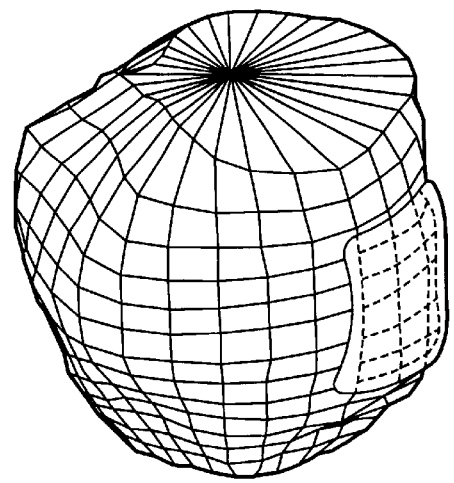
FIG. 2 is an illustration of an example of a display according to one embodiment of the present invention in which a figure image and a functional image are combined.

FIG. 2 shows a display example of a combined image of three dimensional figure image data in a wire frame model about left-side chambers of a heart and three dimensional functional image data concerning a reflux portion in a heart-chamber. The three dimensional figure data shows a figure of an interior wall of the left-side chambers of a heart in the wire frame model. The functional image does not interrupt the figure image. A position having unusual function, such as infarction and reflux, can be recognized in the context of the wire frame model.

Next, the case of displaying functional information by a bull's eye map method is described.

If a bull's eye map type display is selected by means of a separately located operation panel, the application processor 20 forms the bull's eye map type functional image for showing the function of the heart based on the three dimensional functional image data produced by the 3D processor 19. The image data of the bull's eye map is transmitted to the display unit 8 and a combined image of the three dimensional figure image data produced by the 3D processor 19 and the three dimensional functional image data is displayed by the display device 3.

Figure 3A:
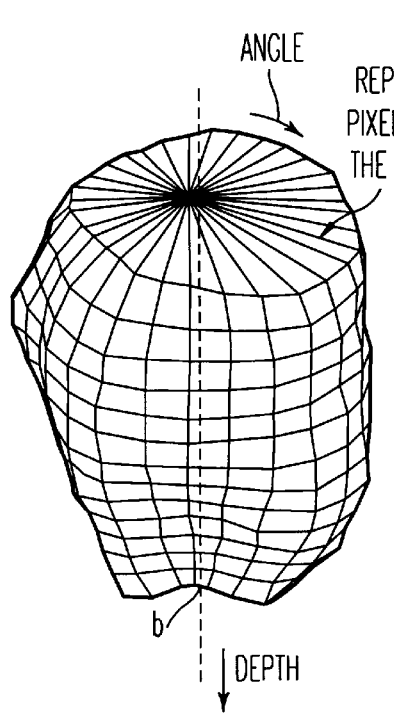
FIG. 3 is an illustration of an example of another combined display according to another embodiment of the present invention.
Figure 3B:
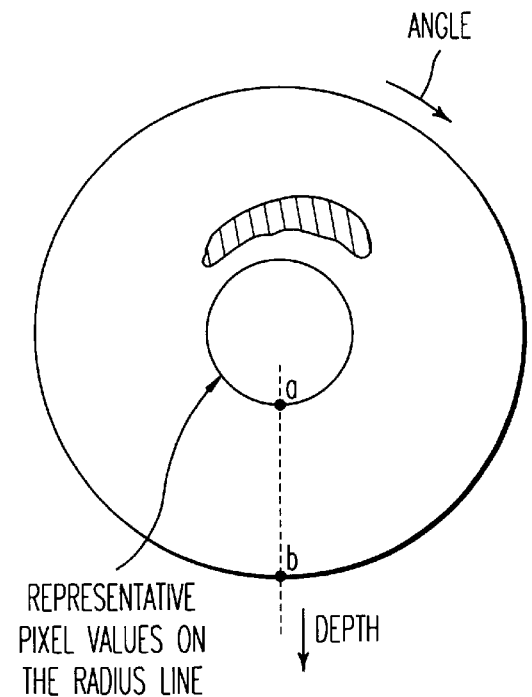

FIG. 3 shows a display example of a combined image of three dimensional figure data and three dimensional functional image data. In FIG. 3, the bull's eye map is displayed to the right of a wire mesh image combining three dimensional functional data positioned on the three dimensional figure data.

The bull's eye map is a map in which the functional information of the heart is displayed by means of a coaxial map in which a point is positioned on a polar coordinate formed by depth and angle. In the context of the bull's eye map, "depth" means position in a cross sectional position of the heart. A distance from a center of the bull's eye map is corresponds to depth. In FIG. 3, the inner most diameter and the outer most diameter of the bull's eye map means the automatically extracted highest point (a) and the lowest point (b), respectively, on the cross sectional surface of the heart. Regarding the angle, the center of gravity of the heart-chamber on the cross sectional surface of the heart is designated as a center and a position of each heart muscle is shown by an angular direction and corresponding to an angular direction with respect to the center of the bull's eye map.

Values displayed on the bull's eye map are typically values such as the highest value or the average value of pixels adjacent to an interior surface automatically extracted, for example, from pixels located within 1 cm from the interior surface. Such values may be tissue moving speed values obtained by the TDI method, for instance spatially differential values of the tissue moving speed values, thereby to indicate the actuation condition of an interior wall of the heart. Also, other values, for example as obtained by the HI method, can be displayed on the bull's eye map. Such a bull's eye map indicates the blood flow condition of an interior wall of the heart. Furthermore, values displayed on the bull's eye map are typically thresholded values obtained by thresholding the TDI or HI values so that portions having low values are detected and distinguishably displayed. Low values of TDI data may indicate infarction, while low values of HI data may indicate blockage of a blood vessel. The condition of an interior wall of the heart is determined based on thresholding of speed values in the tissue Doppler image, and thresholding of brightness values in the harmonic image. In such an example, a location having unusual functioning, such as infarction and reflux, can be recognized without the functional image being interrupted or obstructed by the figure image.

When displaying the HI image, both color coded and monochrome colored display may be employed. In case of a color coded HI display, different colors are assigned to the different amounts of contrast medium detected based on the reflected second harmonic signals. In case of using monochrome coded display, different intensities are assigned to the different amounts of contrast medium detected based on the reflected second harmonic signals.

Figure 4:
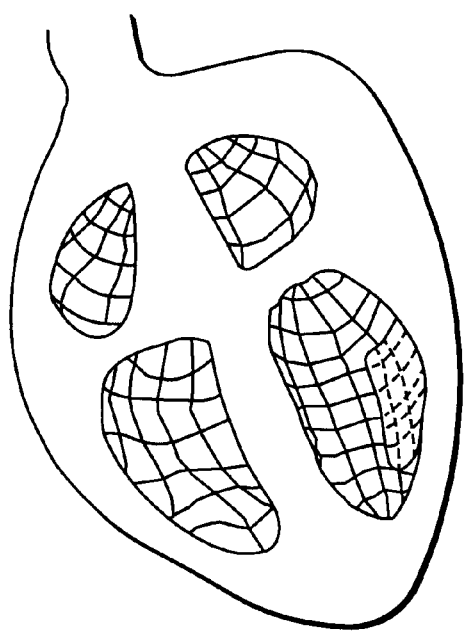
FIG. 4 is an illustration of an example of yet another combined display according to another embodiment of the present invention.

FIG. 4 shows a display example in which the functional image is combined with a figure image of all four chambers in a heart including an interior wall of a left chamber and an outer figure of the heart automatically extracted with wire frame, similar to the example shown in FIG. 2. In the example, a location having unusual function, such as infarction and reflux, can be recognized without the functional image being interrupted by the figure image.

In the above described embodiments, a wire frame method and a bull's eye map method are described as examples of methods of showing a three dimensional figure image. However, it is possible to display a surface model, in which a semi-transparent parameter is included, combined with a functional image. In that case, a location having unusual function, such as infarction and reflux, can also be recognized without the functional image being interrupted by the figure image. Although the invention has been explained in relation to its preferred embodiment, it is to be understood that many other possible modifications and variations can be made without departing from the sprit.

In accordance with the invention, a three dimensional figure of a specific organ can be displayed by a wire frame method, a bull's eye map method and a semi-transparent surface model method. The three dimensional figure of the specific organ is combined with a functional image of the specific organ. The figure image and the functional image are not visually interrupted by each other, that is, one image does not obstruct the other image so that the figure image of the organ can be utilized as a positioning guide for selection of the position of the functional image of the organ.

Obviously, numerous modifications and variations of the present invention are possible in light of the above teachings. It is therefore to be understood that within the scope of the appended claims, the invention may be practiced otherwise than as specifically described herein.

What is new and desired to be secured by Letters Patent of the United States is:

1. An ultrasonic diagnostic apparatus comprising:
   an ultrasonic probe;
   first means for scanning a three dimensional region of a detected object with ultrasonic beams by driving said ultrasonic probe and receiving echo signals reflected from an object within said three dimensional region;
   second means for detecting an organ of said object and forming three dimensional figure image data depicting a figure of the detected organ in said three dimensional region based on the received echo signals; and
   third means for determining a function of the detected organ and forming three dimensional functional image data depicting said function of said detected organ in said three dimensional region based on the received echo signals; and
   fourth means for displaying said three dimensional figure image data combined with said three dimensional functional image data.

2. The apparatus of claim 1, wherein said second means forms three dimensional figure image data representative of an outer figure of said detected organ.

3. The apparatus of claims 1 or 2, wherein said second means forms three dimensional figure image data representative of a wire frame model of said detected organ.

4. The apparatus of claim 3, wherein said second means comprises means for forming a bull's eye map image depicting a function of said detected organ in said three dimensional region for display by said fourth means.

5. The apparatus of claim 3, wherein said third means comprises means for forming tissue Doppler image data representative of a Doppler image.

6. The apparatus of claim 4, wherein said third means comprises means for forming tissue Doppler image data representative of a Doppler image.

7. The apparatus of claim 3, wherein said third means comprises means for forming harmonic image data representative of a harmonic image.

8. The apparatus of claims 1 or 2, wherein said second means forms three dimensional figure image data representative of a semi-transparent surface model of said detected organ.

9. The apparatus of claim 8, wherein said second means comprises means for forming a bull's eye map image depicting a function of said detected organ in said three dimensional region for display by said fourth means.

10. The apparatus of claim 8, wherein said third means comprises means for forming tissue Doppler image data representative of a Doppler image.

11. The apparatus of claim 9, wherein said third means comprises means for forming tissue Doppler image data representative of a Doppler image.

12. The apparatus of claim 11, wherein said third means comprises means for comparing the tissue Doppler image data with a threshold level to derive said three dimensional functional image data.

13. The apparatus of claim 8, wherein said third means comprises means for forming harmonic image data representative of a harmonic image.

14. The apparatus of claims 1 or 2, wherein said second means comprises means for forming a bull's eye map image depicting a function of said detected organ in said three dimensional region for display by said fourth means.

15. The apparatus of claim 14, wherein said third means comprises means for forming tissue Doppler image data representative of a Doppler image.

16. The apparatus of claim 14, wherein said third means comprises means for forming harmonic image data representative of a harmonic image.

17. The apparatus of claim 16, wherein said third means comprises means for comparing the harmonic image data with a threshold level to derive said three dimensional functional image data.

18. The apparatus of claims 1 or 2, wherein said third means comprises means for forming tissue Doppler image data representative of a Doppler image.

19. The apparatus of claim 18, wherein said third means comprises means for comparing the tissue Doppler image data with a threshold level to derive said three dimensional functional image data.

20. The apparatus of claims 1 or 2, wherein said third means comprises means for forming harmonic image data representative of a harmonic image.

21. The apparatus of claim 20, wherein said third means comprises means for comparing the harmonic image data with a threshold level to derive said three dimensional functional image data.

* * * * *